United States Patent
Yada et al.

(10) Patent No.: US 7,258,766 B2
(45) Date of Patent: Aug. 21, 2007

(54) METHOD FOR COLLECTING ACRYLIC ACID

(75) Inventors: Shuhei Yada, Yokkaichi (JP);
Kimikatsu Jinno, Yokkaichi (JP);
Yasushi Ogawa, Yokkaichi (JP);
Yoshiro Suzuki, Yokkaichi (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 10/828,340

(22) Filed: Apr. 21, 2004

(65) Prior Publication Data

US 2004/0195085 A1    Oct. 7, 2004

Related U.S. Application Data

(63) Continuation of application No. PCT/JP02/11377, filed on Oct. 31, 2002.

(30) Foreign Application Priority Data

Nov. 6, 2001  (JP) .............................. 2001-340300

(51) Int. Cl.
*B01D 3/38*     (2006.01)
*B01D 3/42*     (2006.01)
*C07C 51/42*    (2006.01)
*C07C 57/04*    (2006.01)

(52) U.S. Cl. ..................... 203/1; 203/2; 203/3; 203/96; 203/29; 203/DIG. 21; 203/DIG. 25; 562/532; 562/600

(58) Field of Classification Search ................ 203/1–3, 203/95–96, 29, DIG. 21, DIG. 25; 562/532, 562/600
See application file for complete search history.

(56) References Cited

U.S. PATENT DOCUMENTS

| 3,926,744 | A | * | 12/1975 | Noll et al. ..................... 203/55 |
| 4,147,721 | A | * | 4/1979 | Leacock ..................... 562/532 |
| 5,785,821 | A |   | 7/1998 | Sakamoto et al. ............. 203/57 |
| 5,897,749 | A | * | 4/1999 | Kroker et al. .................. 203/2 |
| 6,407,287 | B2 |   | 6/2002 | Matsumoto et al. |
| 6,566,551 | B2 |   | 5/2003 | Nishimura et al. |
| 6,968,872 | B2 | * | 11/2005 | Sakakura et al. ......... 141/311 A |
| 2006/0211886 | A1 | * | 9/2006 | Yada et al. .................. 562/600 |

FOREIGN PATENT DOCUMENTS

| EP | 0 695 736 | * | 7/1996 |
| EP | 1 066 872 |   | 1/2001 |
| EP | 1 070 700 |   | 1/2001 |
| JP | 47-10614  |   | 5/1972 |
| JP | 63-93747  |   | 4/1988 |
| JP | 2001-19655 |   | 1/2001 |
| JP | 2001-220362 |   | 8/2001 |
| JP | 2001-247510 |   | 9/2001 |

* cited by examiner

*Primary Examiner*—Virginia Manoharan
(74) *Attorney, Agent, or Firm*—Wenderoth, Lind & Ponack, L.L.P.

(57) ABSTRACT

A method for collecting acrylic acid is provided, which includes the step of collecting acrylic acid using an aqueous medium from a reaction gas containing acrylic acid obtained by catalytic vapor-phase oxidation of propane, propylene, and/or acrolein, the step being conducted so as to satisfy the following formula (1) (B/A)<1.25 (1) wherein A represents a weight fraction of acrylic acid to all condensable ingredients in the reaction gas before collecting acrylic acid and B represents a weight fraction of acrylic acid in bottoms of a collection device used in the step of collecting. According to the method, acrylic acid can be efficiently collected from the reaction gas containing acrylic acid obtained by catalytic vapor-phase oxidation.

10 Claims, 1 Drawing Sheet

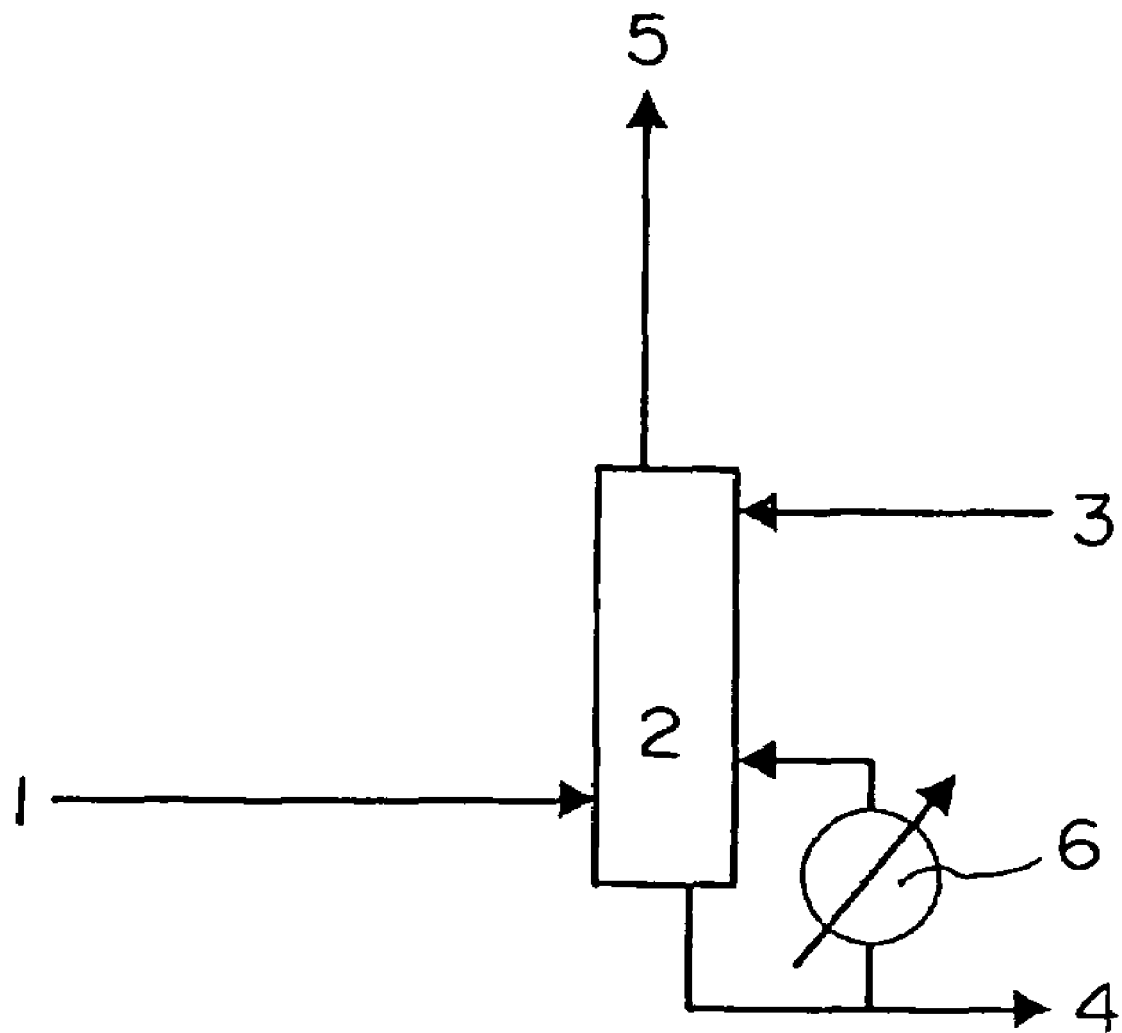
F I G. 1

METHOD FOR COLLECTING ACRYLIC ACID

This application is a Rule 1.53(b) Continuation of PCT/JP02/11377 filed Oct. 31, 2002.

TECHNICAL FILED

The present invention relates to a method for collecting acrylic acid, in particular, a method for collecting acrylic acid in which acrylic acid is collected using a solvent from a gas comprising acrylic acid obtained by catalytic vapor-phase oxidation of propane, propylene, or the like.

BACKGROUND ART

Acrylic acid can be produced by catalytic vapor-phase oxidation of propane, propylene, acrolein, or the like and obtained by a method for collecting acrylic acid from a gas comprising acrylic acid using a collection solvent.

The conventional methods for the collection of acrylic acid using a solvent from a gas comprising acrylic acid include a method for collecting using water or an aqueous solution as a collection solvent.

In such a collection of acrylic acid using the aqueous solution from the gas comprising acrylic acid, a problem has occurred in that part of acrylic acid is entrained in the moisture contained in the gas discharged from a collection device instead of being collected, and then discharged together therewith.

To solve the problem, studies have been conducted on shape and arrangement of materials in a collection device, the composition of an aqueous solution used for the collection, and so on (e.g., JP 13-19655 A and JP 09-157213 A). However, acrylic acid distilled from the top of the collection column is influenced by operation conditions, so that it is difficult to suppress the loss of acrylic acid from the top of the column stably over long periods. Moreover, the method for employing high-performance packing as materials in the collection device is not a satisfactory method because there is a problem in that clogging tends to occur owing to the polymerization of acrylic acid when acrylic acid is distilled toward the top of the column in an increased amount along with variations in the operation.

DISCLOSURE OF INVENTION

The present invention has been made in view of the above problems and has an object to provide a method for collecting acrylic acid, where a concentration of acrylic acid remaining in a gas comprising acrylic acid is lowered in collecting acrylic acid from the gas using a collection device.

For solving the above problems, as a result of conducting various studies, the inventors of the present invention have found out that, at the time of collection, the concentration of acrylic acid remaining in the gas is closely related to both the weight fraction of acrylic acid to all condensable ingredients in the reaction gas before collection and the weight fraction of acrylic acid to the bottoms of a collection device used in a step of collecting.

That is, the present invention provides the following.

(1) A method for collecting acrylic acid comprising the step of collecting acrylic acid using an aqueous medium from a reaction gas comprising acrylic acid obtained by catalytic vapor-phase oxidation of propane, propylene, and/or acrolein, wherein: the following formula (1) is satisfied if A represents a weight fraction of acrylic acid to all condensable ingredients in the reaction gas before collecting acrylic acid and B represents a weight fraction of acrylic acid in a bottoms of a collection device used in the step of the collecting.

$$(B/A)<1.25 \qquad (1)$$

(2) The method for collecting acrylic acid as described in the item (1), wherein the aqueous medium is an aqueous solution that comprises 90 wt % or more of water. (3) The method for collecting acrylic acid as described in the item (1) or (2), wherein the collection device used in the step of collecting is a column-type collection device comprising a collection column. (4) The method for collecting acrylic acid as described in any one of the items (1) to (3), wherein the collection is performed while a temperature of a top of the collection column of the column-type collection device is kept within a predetermined range.

Industrially, acrylic acid of the present invention is usually obtained by the so-called catalytic vapor-phase oxidization which oxidizes propane, propylene, and/or acrolein by molecular oxygen in the presence of a solid catalyst.

More specifically, there are a method for directly producing acrylic acid by reacting propylene with a molecular-oxygen-containing gas such as the air in the presence of a molybdenum-oxide solid oxidation catalyst (single-step process: see, e.g., JP 7-53448 A), a method for producing acrylic acid by reacting propylene with molecular oxygen in the presence of a molybdenum-oxide solid oxidation catalyst at a first reaction zone to obtain acrolein and reacting acrolein with molecular oxygen in the presence of a molybdenum-oxide solid oxidation catalyst at a second reaction zone (two-step process: see, e.g., JP 47-10614 A or JP 63-93747 A). The methods described therein can be preferably used in the present invention.

In the present invention, as acrylic acid obtained as described above is in an acrylic-acid-containing gaseous state, acrylic acid is obtained as an aqueous solution comprising acrylic acid by bringing acrylic acid into contact with an aqueous medium to separate and collect it from a reaction gas. In this case, preferably, provided that A represents a weight fraction of acrylic acid to all condensable ingredients in the reaction gas before collection of acrylic acid and B represents a weight fraction of acrylic acid in a bottoms of a collection device used in the step of collecting, the following formula (1) is satisfied:

$$(B/A)<1.25 \qquad (1)$$

Furthermore, the weight fraction A of acrylic acid to all condensable ingredients in the reaction gas before collection of acrylic acid is represented by [the weight of acrylic acid in the reaction gas]/[the weight of all condensable ingredients in the reaction gas].

Under the condition of (B/A)<1.25, the efficiency of collecting acrylic acid in the solvent can be raised. (B/A)<1.1 is more preferable. In addition, B/A can be adjusted by the temperature of the top of the column, the amount of the reaction gas supplied before collection, the amount of the collection solvent used, the moisture content in the collection solvent, or the like.

The weight of acrylic acid to all condensable ingredients in the reaction gas, the weight of all condensable ingredients, and the weight ratio of acrylic acid in the bottoms can be analyzed, for example, by the method for sampling the reaction gas and the bottoms and analyzing them with gas chromatography.

The reaction gas of the present invention is a gas comprising acrylic acid generated by catalytic vapor-phase oxidation generally at a high temperature of about 250 to 300° C., but the gas is preferably cooled at 140 to 250° C., more preferably at 170 to 220° C. before supplying to the collection column.

The solvent used in the method for collecting of the present invention is an aqueous solution that comprises 90 wt % or more of water preferably, more preferably an aqueous solution that comprises 92 wt % or more of water. Ingredients except the water in the collection solvent include formaldehyde, formic acid, acetic acid, and acrylic acid and so on. Using them as the collection solvent increases the efficiency of collecting acrylic acid.

The collection device used in the method for collecting the present invention is preferably a column-type collection device comprising a collection column. The collection columns include, although not particularly limited to, plate- and packing-type collection columns.

In the present invention, in order to set the value of the above B/A to less than 1.25, it is preferable to keep the temperature of the top of the collection column in the column-type collection device within a predetermined range, particularly preferably within the range of ±1° C. relative to the steady operation conditions. For that purpose, the periphery of the bottom or top portion of the column of the column-type collection device may be provided with, for example, a heat-removing device such as a heat-removing coil or an external heat exchanger to control the heat removal. When the temperature of the top of the column is constant, the amount of water (water vapor) distilled from the top of the column can be kept constant and the water concentration of acrylic acid aqueous solution flowed out from the bottom of the column, i.e., the concentration of acrylic acid in the bottoms can be kept constant.

In addition, B/A may be adjusted to a smaller value by the method for (i) increasing the amount of heat removed by the heat-removing device; (ii) increasing the amount of the aqueous medium used as a collection solvent; (iii) lowering the temperature of the reaction gas (140° C. or more at the minimum); or the like. At the time of the steady operation, the method (i) is preferably used.

However, when the value of B/A is set extremely small, an increase in energy load is involved in the step of purifying acrylic acid after the step of collecting. Therefore, the lower limit of B/A is more preferably 0.8, still more preferably 0.9.

In addition, from the viewpoint of avoiding the clogging by polymerization of acrylic acid, the temperature of the bottom of the column is preferably 86° C. or less and the temperature of the top of the column is preferably 72° C. or less.

Hereinafter, an embodiment of the present invention will be described with reference to the drawing. However, the present invention is not limited thereto.

FIG. 1 is a schematic diagram that illustrates an embodiment of the present invention. In FIG. 1, a reaction gas 1 comprising acrylic acid obtained by catalytic vapor-phase oxidation is supplied from the outlet of an oxidation reactor to the bottom of a collection column 2. Before being supplied to the collection column, the reaction gas 1 is cooled preferably to 140 to 250° C., particularly preferably 170 to 220° C. at the outlet of the oxidation reactor or using a heat exchanger (not shown). Acrylic acid may be condensed and polymerized in this line when the gas is cooled to lower than 140° C., which is not desirable because clogging of piping or the like may occur. In contrast, when the temperature is too high, the column diameter of the collection column increases as the volume of the gas and the desired amount of heat removed in the collection column increase, which may easily cause a reduction in collection efficiency as well as an increase in cost of equipment.

When the production of acrylic acid is carried out by the catalytic vapor-phase oxidation of propylene, the resulting reaction gas typically contains acrylic acid, nitrogen, carbon dioxide, oxygen, carbon monoxide, non-condensable hydrocarbon, condensable organic materials, water, and so on. Furthermore, the term "condensable ingredient" used in the present invention means an ingredient in which a pure substance thereof has a boiling point of 20° C. or more and the term "non-condensable" used in the present invention means one in which a pure substance thereof has a boiling point of less than 20° C.

An aqueous solution 3 as a collection solvent is supplied to the top of the collection column. The temperature of the aqueous solution 3 supplied is preferably 20 to 50° C. The water content in the aqueous solution 3 to be supplied is preferably 0.5- to 2-fold of the water content in the reaction gas. The temperature of the aqueous solution supplied is preferably lowered as much as possible, and the temperature is typically 20 to 50° C. If it is lower than 20° C., the costs for cooling, such as the costs of refrigeration facilities may be high and thus it is not so economical. On the other hand, the temperature exceeding 50° C. tends to cause a decrease in collection efficiency.

The weight fraction of acrylic acid to all condensable ingredients in the reaction gas and the weight fraction of acrylic acid in the bottoms should be set such that the value of B/A is less than 1.25. For setting the value of B/A to less than 1.25, the heat removal may be controlled by providing the periphery of the bottom or top portion of the collection column of the column-type collection device with a heat exchanger 6 as described above such that the temperature of the top of the collection column of the column-type collection device is within a predetermined range, particularly ±1° C. relative to the steady operation conditions. Setting the temperature of the top of the column to fall within the predetermined range allows a water (water vapor) 5 distilled from the top of the column can be kept at constant amount, so that the concentration of water in acrylic acid aqueous solution flowing out from the bottom of the column, i.e., acrylic acid content in a bottoms 4 can be kept constant.

The aqueous solution containing acrylic acid collected as described above can result in purified acrylic acid through the ordinary steps conducted in the method for producing acrylic acid, namely, through the step of extracting using an aqueous solution containing acrylic acid and an appropriate extracting solvent, the step of separating the solvent, and the step of purifying.

BRIEF DESCRIPTION OF DRAWINGS

FIG. 1 is a schematic diagram illustrative of an embodiment of a method for collecting of the present invention.

BEST MODE FOR CARRYING OUT THE INVENTION

Hereinafter, the present invention will be described in more detail based on examples and comparative examples. However, the present invention is not limited to the examples described below without departing from the gist of the present invention.

EXAMPLE 1

Propylene was mixed with the air and an inert gas including of water, nitrogen, and carbon dioxide and then reacted with molecular oxygen at a first reaction zone in the presence of a molybdenum-oxide solid catalyst to obtain acrolein. Subsequently, acrolein was reacted with molecular oxygen at a second reaction zone in the presence of a molybdenum-oxide solid catalyst, resulting in a reaction gas that contains 3,200 kg/h of acrylic acid.

<1> Composition of Reaction Gas

<Mole Fraction>
Nitrogen+carbon dioxide 71.6%
Non-condensable ingredients except the above 5.3%
(Specifically, unreacted material propylene, oxygen, carbon monoxide, or the like)
Acrylic acid 6.3%
Water 16.4%
Condensable ingredients except the above 0.4%
(Specifically, acetic acid, maleic acid, or the like)

<Weight Fraction>
Nitrogen+carbon dioxide 68.2%
Non-condensable ingredients except the above 5.8%
Acrylic acid 15.2%
Water 10.0%
Condensable ingredients except the above 0.8%

The weight fraction of acrylic acid in the condensable ingredients in the above reaction gas was 58.5 wt %.

<2> Collection Device

A plate-type collection column was used as a collection device. The reaction gas obtained in the above was cooled to 170° C. by a heat exchanger provided on the line at the outlet of an oxidation reactor and was then supplied to the bottom of the collection column.

There is a line, in which a liquid in the bottom of the column (an aqueous solution comprising acrylic acid and generated in the bottom of the column and provided as bottoms) is circulated on the sixth plate from the bottom and there is a heat exchanger for cooling the circulation liquid in the line.

The collection column used in this example has 36 plates. As a collection solvent, an aqueous solution containing 93 wt % of water and 6 wt % of acetic acid (1% remaining portion is formaldehyde, formic acid, or acrylic acid) was supplied from the top of the column to the collection column at 40° C., followed by operation at 105 kPa in pressure of the top of the column. The volume of water was set equal to that of water in the reaction gas.

It was operated by adjusting the load of the heat exchanger such that the temperature of the top of the collection column reached 60° C.

<3> Results

Acrylic acid in the bottoms collected as described above had a concentration of 61.8 wt % and the loss of acrylic acid from the gas distilled from the top of the column was 0.4%. The operation results are collectively listed in Table 1.

In addition, the loss of acrylic acid was measured as follows. A gas of the top of the column was sampled from the sampling nozzle provided in the piping from the top of the collection column, and then a part thereof liquefied by cooling and the un-liquefied part thereof were subjected to the composition analysis with gas chromatography, respectively. The absolute quantity of each component was calculated from the amount of the gas supplied to the reactor, and the ratio with the sum total with acrylic acid of the liquid in the bottom of the column set to 100% was calculated. Furthermore, gas chromatography was used for the composition of the liquid in the bottom of the column and a flow meter was used for the volume of the liquid in the bottom of the column.

EXAMPLE 2

Acrylic acid was collected under the same conditions as those of Example 1 except that the temperature of the top of the column was set to 63.5° C. The concentration of acrylic acid in the bottoms was 67.5 wt % and the loss of acrylic acid from the gas distilled from the top of the column was 1.9%. The results are shown in Table 1.

COMPARATIVE EXAMPLE 1

Acrylic acid was collected under the same conditions as those of Example 1 except that the temperature of the top of the column was set to 66.5° C. and the operation was conducted for increasing B/A. The concentration of acrylic acid in the bottoms was 73.6 wt % and the loss of acrylic acid from the gas distilled from the top of the column was 5.4%. The results are shown in Table 1.

COMPARATIVE EXAMPLE 2

Acrylic acid was collected under the same conditions as those of Example 1 except that the temperature of the top of the column was set to 66.5° C. and the plates used in the collection column was increased by 10 plates. The concentration of acrylic acid in the bottoms was 74.4 wt % and the loss of acrylic acid from the gas distilled from the top of the column was 4.4%.

The concentration of acrylic acid in the bottoms was elevated by increasing the plate of the collection column. In contrast, a large loss of acrylic acid from the gas distilled from the top thereof was observed. The results are shown in Table 1.

EXAMPLE 3

The collection was performed under the same conditions as those of Example 1 except that the concentration of "nitrogen+carbon dioxide" in the reaction gas was increased by 4 mol % while the water supplied to the collection column was decreased for that, and the temperature of the top of the column was set to 59° C.

At this moment, the concentration of acrylic acid in the condensable ingredients in the reaction gas was 64.7 wt %, acrylic acid concentration in the bottoms was 68.3 wt %, and the loss of acrylic acid from the gas distilled from the top of the column was 0.5%. The results are shown in FIG. 1.

COMPARATIVE EXAMPLE 3

Acrylic acid was collected under the same conditions as those of Example 3 except that the temperature of the top of the column was set to 65.0° C. The concentration of acrylic acid in the bottoms was 81.3 wt % and the loss of acrylic acid from the gas distilled from the top of the column was 5.3%. The results are shown in Table 1.

EXAMPLE 4

Acrylic acid was collected under the same conditions as those of Example 1 except that the temperature of the top of the column was set to 66.5° C. and the volume of water in the aqueous solution used for the collection was 1.5-fold of the volume of water in the reaction gas. A concentration of acrylic acid in the bottoms was 61.8 wt % and the loss of acrylic acid from the gas distilled from the top of the column was 0.3%. The results are shown in Table 1.

COMPARATIVE EXAMPLE 4

Acrylic acid was collected under the same conditions as those of Example 4 except that the temperature of the top of the column was set to 71.0° C. The concentration of acrylic acid in the bottoms was 73.7 wt % and the loss of acrylic acid from the gas distilled from the top of the column was 3.8%. The results are shown in Table 1.

EXAMPLE 5

Acrylic acid was collected under the same conditions as those of Example 1 except that the temperature of the top of the column was set to 55.5° C. and the volume of water in the aqueous solution used for the collection was 0.7-fold of the volume of water in the reaction gas. The concentration of acrylic acid in the bottoms was 63.0 wt % and the loss of acrylic acid from the gas distilled from the top of the column was 0.9%. The results are shown in Table 1.

COMPARATIVE EXAMPLE 5

Acrylic acid was collected under the same conditions as those of Example 5 except that the temperature of the top of the column was set to 62.0° C. The concentration of acrylic acid in the bottoms was 73.8 wt % and the loss of acrylic acid from the gas distilled from the top of the column was 4.3%. The results are shown in Table 1.

INDUSTRIAL APPLICABILITY

According to the present invention, at the time of collecting acrylic acid with an aqueous medium, acrylic acid can be efficiently collected while the concentration of acrylic acid remaining in a gas is reduced.

The invention claimed is:
1. A method for collecting acrylic acid comprising:
 (1) providing a collection column to which a first, second, third, fourth and fifth lines are respectively connected, wherein
  a first line is connected at the bottom of the collection column;
  a second line is connected to the collection column at a higher position than the bottom;
  a third line is connected to the first line and to the collection column at a higher position than the position where the second line is connected, and has a heat-removing device;
  a fourth line is connected to the collection column at a higher position than the position where the third line is connected; and,
  a fifth line is connected at the top of the collection column, which is a higher position than the position where the fourth line is connected;
 (2) introducing a reaction gas from the second line into the collection column at a temperature of 140 to 250° C., the reaction gas comprising acrylic acid obtained by catalytic vapor-phase oxidation of propane, propylene, and/or acrolein;
 (3) introducing an aqueous medium from the fourth line into the collection column at a temperature of 20 to 50° C. whereby the acrylic acid in the reaction gas is collected in the aqueous medium to produce an acrylic acid aqueous solution;
 (4) causing the acrylic acid aqueous solution as bottoms to flow out from the bottom of the collection column through the first line;

TABLE 1

|  | Flow rate of Acrylic acid in top of column (kg/h) | Flow rate of bottoms (kg/h) | Acrylic acid in bottom of column | | Loss from top of column (%) | B/A |
| --- | --- | --- | --- | --- | --- | --- |
|  |  |  | Concentration (wt %) | Flow rate (kg/h) |  |  |
| Example 1 | 12 | 5110 | 61.8 | 3158 | 0.4 | 1.06 |
| Example 2 | 60 | 4600 | 67.5 | 3105 | 1.9 | 1.15 |
| Comparative Example 1 | 172 | 4070 | 73.6 | 2995 | 5.4 | 1.26 |
| Comparative Example 2 | 140 | 4090 | 74.4 | 3043 | 4.4 | 1.27 |
| Example 3 | 16 | 4620 | 68.3 | 3155 | 0.5 | 1.06 |
| Comparative Example 3 | 169 | 3700 | 81.3 | 3008 | 5.3 | 1.26 |
| Example 4 | 9 | 5150 | 61.8 | 3183 | 0.3 | 1.06 |
| Comparative Example 4 | 121 | 4220 | 73.7 | 3110 | 3.8 | 1.26 |
| Example 5 | 28 | 5000 | 63.0 | 3150 | 0.9 | 1.08 |
| Comparative Example 5 | 137 | 4150 | 73.8 | 3066 | 4.3 | 1.26 |

The flow rate of acrylic acid in the bottom of the column is equal to [the flow rate of the liquid in the bottom of the column]×[the concentration of acrylic acid in the bottom of the column]; and the loss from the top of the column is equal to [the flow rate of acrylic acid in the top of the column]/[(the flow rate of acrylic acid in the top of the column)+(the flow rate of acrylic acid in the bottom of the column)]×100(%).

(5) causing the reaction gas remaining after the collection step to flow out from the top of the collection column through the fifth line;
 (6) introducing the acrylic acid aqueous solution of the first line into the collecting column through the third line; and
 (7) performing heat removal in the collection column by using the heat-removing device to maintain the following condition: 0.8<(B/A)<1.25, wherein A represents a weight fraction of acrylic acid to all condensable ingredients in the reaction gas before collecting acrylic acid and B represents a weight fraction of acrylic acid in the bottoms.

2. The method according to claim 1, wherein the aqueous medium introduced from the fourth line into the collection column is an aqueous solution that comprises at least 90 wt % of water.

3. The method according to claim 1, wherein the temperature at the top of the collection column is 72° C. or less, and the temperature of the bottom at the collection column is 86° C. or less.

4. The method according to claim 1, wherein a water content in the aqueous medium introduced from the fourth line into the collection column is 0.5- to 2-fold of a water content in the reaction gas introduced into the collection column.

5. The method according to claim 1, wherein a degree of fluctuation of the temperature at the top of the collection column is within 2° C. in steady operation conditions.

6. The method according to claim 5, wherein the temperature at the top of the collection column is kept within ±1° C. of a temperature in steady operation conditions.

7. The method according to claim 1, wherein the aqueous medium introduced from the fourth line into the collection column comprises at least 90 wt % of water, and the water content in the aqueous medium is 0.5- to 2-fold of a water content in the reaction gas introduced into the collection column.

8. The method according to claim 7, wherein a degree of fluctuation of the temperature at the top of the collection column is within 2° C. in steady operation conditions.

9. The method according to claim 8, wherein the temperature at the top of the collection column is kept within ±1° C. of a temperature in steady operation conditions.

10. The method according to claim 1, wherein the aqueous medium introduced from the fourth line into the collection column comprises at least 90 wt % of water, wherein the water content in the aqueous medium is 0.5- to 2-fold of a water content in the reaction gas introduced into the collection column, and B/A is $0.8 < (B/A) \leq 1.15$.

* * * * *